(12) United States Patent
Detamore et al.

(10) Patent No.: US 8,293,510 B2
(45) Date of Patent: Oct. 23, 2012

(54) METHOD OF PREPARING A HYDROGEL NETWORK ENCAPSULATING CELLS

(75) Inventors: Michael Detamore, Lawrence, KS (US); Stevin H. Gehrke, Lawrence, KS (US)

(73) Assignee: University of Kansas, Lawrence, KS (US)

( * ) Notice: Subject to any disclaimer, the term of this patent is extended or adjusted under 35 U.S.C. 154(b) by 1271 days.

(21) Appl. No.: 11/985,707

(22) Filed: Nov. 16, 2007

(65) Prior Publication Data
US 2009/0130755 A1 May 21, 2009

(51) Int. Cl.
*C12N 11/10* (2006.01)
*C12N 11/04* (2006.01)
*C12N 11/02* (2006.01)

(52) U.S. Cl. .................. 435/178; 435/177; 435/182

(58) Field of Classification Search .................. None
See application file for complete search history.

(56) References Cited

U.S. PATENT DOCUMENTS

| | | | |
|---|---|---|---|
| 4,774,093 A * | 9/1988 | Provonchee et al. | 424/493 |
| 4,997,443 A * | 3/1991 | Walthall et al. | 623/23.72 |
| 6,497,902 B1 | 12/2002 | Ma | |
| 6,699,470 B1 * | 3/2004 | Ameer et al. | 424/93.7 |
| 7,022,313 B2 * | 4/2006 | O'Connor et al. | 424/48 |
| 7,151,124 B2 * | 12/2006 | Kovar et al. | 522/104 |
| 2003/0012816 A1 | 1/2003 | West et al. | |
| 2004/0116305 A1 | 6/2004 | Osada et al. | |
| 2005/0147685 A1 | 7/2005 | Osada et al. | |
| 2006/0003442 A1 | 1/2006 | Gong et al. | |
| 2006/0084159 A1 | 4/2006 | Trubetskoy | |
| 2006/0246113 A1 | 11/2006 | Griffith et al. | |
| 2007/0048291 A1 | 3/2007 | Mang et al. | |

FOREIGN PATENT DOCUMENTS
EP 1 498 437 1/2005

OTHER PUBLICATIONS

Eichler et al., *Insect Cuticle as Biomimetic Material*, AIChE Annual Meeting and Fall Conference (Oct. 31, 2005).
Kadakia et al., *Increased Stem Cell Adhesion in a 3-D Semi-Interpenetrating Network*, BMES Chicago, IL (Oct. 12, 2006) [abstract].
Lomakin et al., *Insect Cuticle as a Motif for Biomimetic Materials*, AIChE Annual Meeting San Francisco, CA PowerPoint presentation (Nov. 16, 2006).
Roatch et al., *Bio-inspired Hydrogels for Cartilage Tissue Engineering*, Undergraduate Research Symposium PowerPoint presentation, University of Kansas (Apr. 14, 2007).
Roatch et al., *High toughness bio-inspired hydrogels for cartilage tissue engineering*, Table of Contents, University of Kansas, Undergraduate Research Symposium, Apr. 14, 2007.
Roatch et al., *High toughness bio-inspired hydrogels for cartilage tissue engineering*, Presentation, University of Kansas, Undergraduate Research Symposium, Apr. 14, 2007 [abstract].

\* cited by examiner

*Primary Examiner* — David Naff
(74) *Attorney, Agent, or Firm* — Stinson Morrison Hecker LLP (57) ABSTRACT

The present invention is directed to a hydrogel network comprised of a physically cross-linked polymer and a chemically cross-linked polymer or physically entangled copolymer containing living cells, such as chondrocytes, encapsulated therein. In a preferred aspect, the physically cross-linked polymer is selected from the group consisting of thermally gelling polysaccharides and proteins, such as agarose or gelatin, and the chemically cross-linked or physically entangled polymer is synthesized from a water-soluble vinyl monomer, either as a homopolymer or copolymer, such as polyethylene glycol diacrylate ("PEG-DA") and 2-hydroxyethyl methacrylate ("HEMA").

21 Claims, 6 Drawing Sheets

METHOD OF PREPARING A HYDROGEL NETWORK ENCAPSULATING CELLS

STATEMENT REGARDING FEDERALLY SPONSORED RESEARCH OR DEVELOPMENT

The present invention was supported in part by NSF Grant No. MCB026039 and NIH Grant No. 1 R21 EB008783-01, and the government may have certain rights in the invention.

CROSS-REFERENCE TO RELATED APPLICATIONS

Not applicable.

BACKGROUND OF THE INVENTION

Polymer gels possess a number of interesting properties which solids or liquids cannot singly have. However, when an attempt is made to utilize such gels for consumer applications or in the medical and industrial fields, their primary limitation in performance is often inadequate mechanical strength. This is particularly true in tissue engineering applications where cells must be encapsulated in a hydrogel prior to implantation in the body in the desired site to regenerate damaged or diseased tissues.

Recently, research has involved so-called "dual network" structures potentially arranged as either interpenetrating networks ("IPNs") or as semi-IPNs. Recent work by Gong, Osada, and coworkers illustrated the potential of such polymer systems tested under compression. See Gong et al., *Double-Network Hydrogels with Extremely High Mechanical Strength*, Advanced Materials 15(14) 1155-1158 (2003); Na et al., *Structural Characteristics of Double Network Gels with Extremely High Mechanical Strength*, Macromolecules 37(14) 5370-5374 (2004); Osada et al., U.S. Patent Application No. 2005/0147685 titled "Hydrogel of (Semi) Interpenetrating Network Structure and Process for Producing the Same"; Gong et al., U.S. Patent Application No. 2006/0003442 titled "Cell Culture Scaffold, Methods of Manufacturing the Scaffold and Cell Culture Methods"; Osada et al., U.S. Patent Application No. 2004/0116305 titled "Low Friction Hydrogel Having Straight Chain Polymers and Method for Preparation Thereof." In addition, the present inventors investigated PAMPS/PAAm, poly(2-acrylamido-2-methyl-propanesulfonic acid) ("PAMPS")/polyacrylamide ("PAAm"), and agarose/poly(2-hydroxyethyl methacrylate) ("PHEMA") as two IPN and semi-IPN gels as synthetic model analogs to insect cuticle. In those experiments, the agarose/PHEMA network gel was irradiated by UV light for about 6 to 24 hours which yielded a maximum fracture stress of 0.65±0.5 MPa with a fracture strain of 201±33% at a water content of approximately 79%. See Eichler et al., Abstract, *Insect Cuticle as a Motif for Biomimetic Materials*, in Proceedings of the 2005 AIChE Annual Meeting (Oct. 31, 2005).

The present invention is directed to an improved hydrogel network, and in particular one that is well adapted to maintain viability of mammalian cells encapsulated therein.

BRIEF SUMMARY OF THE INVENTION

The present invention is directed to a hydrogel network comprised of a physically cross-linked polymer and a chemically cross-linked or physically entangled polymer or copolymer containing living cells encapsulated therein. In a preferred aspect, the physically cross-linked polymer is selected from the group consisting of thermally gelling polysaccharides such as agarose or thermally gelling proteins such as gelatin, and the chemically cross-linked or physically entangled polymer or copolymer is synthesized from a water-soluble vinyl monomer such as polyethylene glycol diacrylate ("PEG-DA") and 2-hydroxyethyl methacrylate ("HEMA"), either as a homopolymer or copolymer. Thus, the network is comprised of at least two chemically distinct but physically interlocked networks having living cells encapsulated therein.

The present invention is also directed to a method for manufacturing hydrogel networks comprising a physically cross-linked polymer and a chemically cross-linked or physically entangled polymer or copolymer having living cells encapsulated therein. The preferred method comprises the step of forming a solution of agarose, gelatin, or other suitable thermally gelling polysaccharide or protein (with an optional initiator, such as a photoinitiator, that will be useful in the next step) at a temperature in which the cells are viable (about 20° C. to 60° C., but typically 30° C. to 50° C.) and dispersing the living cells therein; cooling the agarose or gelatin solution or other suitable thermally gelling polysaccharide or protein down to or below its gelation temperature in which the living cells are also viable to encapsulate the cells in the agarose or gelatin gel; contacting the agarose or gelatin gel having the living cells encapsulated therein with a solution comprising PEG-DA or HEMA (with an optional initiator, such as a photoinitiator, if not included during the previous gelation step) for a sufficient period of time to disperse the PEG-DA or HEMA within the gel; and then cross-linking and/or polymerizing the PEG-DA or HEMA to form higher molecular weight networks (as in the bi-functional PEG-DA, thus forming an IPN) or polymers (as in the mono-functional HEMA, thus forming a semi-IPN). A bi-functional or multi-functional cross-linker (e.g., a monomer having more than one vinyl group) may optionally be added to the solution comprising the monofunctional monomers like HEMA to form a PHEMA network and thus an IPN. Alternatively, the bi-functional or multifunctional cross-linker may be added to the agarose or gelatin solution prior to gelation. Preferred bi-functional or multi-functional cross-linkers include PEG-DA and N,N'-methylene-bis-acrylamide.

In one aspect, the step of forming the solution of agarose or gelatin or other suitable thermally gelling polysaccharide or protein at a temperature in which the living cells are viable occurs at a temperature of about at about 35° C. to 45° C., and most preferably at about 37° C.

In another aspect, the agarose or gelatin gel or other suitable thermally gelling polysaccharide or protein is formed by thermal gelation, and then soaked in a PEG-DA or HEMA solution along with a suitable photoinitiator (which may be in the agarose or gelatin gel or in the PEG-DA or HEMA solution). In the case of a HEMA solution, a suitable cross-linker is optionally added to the HEMA solution or to the agarose or gelatin gel to form an IPN rather than the semi-IPN that will be formed in its absence. The PEG-DA or HEMA solution penetrates and disperses throughout the agarose or gelatin gel or other suitable thermally gelling polysaccharide or protein. When irradiated with light which activates the photoinitiator (typically ultraviolet light), the PEG-DA or HEMA polymerizes and/or cross-links into a network that penetrates and is entangled throughout the agarose or gelatin network, but is not covalently linked to the agarose, gelatin, or other polysaccharide or protein network.

In another aspect, the PEG-DA or HEMA is preferably polymerized and/or cross-over linked over a period of time so that that a substantial portion of the living cells remain viable. Typically, the cells are irradiated for less than about one hour, and still more preferably less than about 50, 40, 30, 20, 10, 9, 8, 7, 6, 5, 4, 3, 2, or 1 minutes.

The hydrogel networks having living cells encapsulated therein have high mechanical strength, and much higher than either of the single networks independently, and can be used in a very versatile manner, such as in implants or prostheses.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

DETAILED DESCRIPTION OF PREFERRED EMBODIMENT

The present invention is directed to a hydrogel network comprised of a physically cross-linked polymer and a chemically cross-linked or physically entangled polymer or copolymer containing living cells encapsulated therein. Thus, the network is comprised of at least two chemically distinct but physically interlocked networks, having living cells encapsulated therein.

As used herein, the term "encapsulated" implies that the cells reside primarily within the interior of the hydrogel network as opposed to merely residing upon or attaching to the surface of the hydrogel network. The concentration of cells may be as low as a single cell, but is preferably about 1,000,000 cells/cm$^3$ or more to 50,000,000 cells/cm$^3$ or more throughout the total gel volume.

The present invention is also directed to a method for manufacturing hydrogel networks comprising a physically cross-linked polymer and a chemically or physically entangled cross-linked polymer or copolymer having living cells encapsulated therein. The preferred method comprises the step of forming a solution of agarose or gelatin (with an optional initiator, such as a photoinitiator, and/or cross-linker) at a temperature in which the cells are viable (typically about 30° C. to 60° C.) and dispersing the living cells therein; cooling the agarose or gelatin solution to its gelation temperature in which the living cells are also viable to encapsulate the cells in an agarose or gelatin gel; contacting the agarose or gelatin gel having the living cells encapsulated therein with a solution comprising PEG-DA or HEMA (with an optional initiator, such as a photoinitiator and/or cross-linker) for a sufficient period of time to disperse the PEG-DA or HEMA within the gel; and then polymerizing and/or cross-linking the PEG-DA or HEMA.

The step of forming the solution of agarose or gelatin at a temperature in which the living cells are viable occurs at a temperature of about at about 35° C. to 45° C., and most preferably at about 37° C.

In one aspect, the agarose or gelatin gel is formed by thermal gelation, and then soaked in a PEG-DA or HEMA solution along with a suitable initiator, such as a photoinitiator. In another aspect, the photoinitiator is added to the agarose or gelatin solution prior to gelation. When irradiated with ultraviolet light, the PEG-DA or HEMA polymerizes and/or cross-links into a polymer or network that penetrates through the agarose or gelatin network, but is not covalently linked to the agarose or gelatin network.

In still another aspect, the agarose or gelatin gel having the living cells encapsulated therein is contacted (e.g., soaked) with the PEG-DA or HEMA solution for a period of time that is sufficient to permit these molecules to disperse or penetrate at least partially through the gel. Typically, the gel is soaked within the PEG-DA or HEMA solution for a period of time between about 2 and 60 hours, more preferably between about 6 and 48 hours, and still more preferably between about 12 and 36 hours, and most preferably for about 24 hours.

The PEG-DA or HEMA is preferably polymerized and/or cross-linked over a period of time so that that a substantial portion of the living cells remain viable. Typically, the cells are irradiated for less than about one hour, and still more preferably less than about 50, 40, 30, 20, 10, 9, 8, 7, 6, 5, 4, 3, 2, or 1 minutes.

In the present invention, the physically cross-linked gel is preferably selected from the group consisting of thermally gelling polysaccharides such as agarose or thermally gelling proteins such as gelatin. Agarose is a natural polymer extracted from seaweed, and varies in its properties (molecular weight, precise chemical composition, side chains, etc.) and may be chemically functionalized to alter desirable properties such as the gelation temperature. Further, while commercially available agarose gels have a variety of EEO values when used for electrophoresis, such properties should not be critical in the present invention. Other potentially useful thermally gelling polysaccharides include kappa-carrageenan and iota-carrageenan. Gelatin is a protein derived from collagen from a wide variety of animal tissues and species. Like agarose, the properties of gelatin such as molecular weight and precise chemical composition are variable, yet the invention is not strongly dependent upon the exact compositions. Furthermore, there are other thermally gelling proteins that are potentially useful in this invention, such as elastin-mimetic protein polymers and silk-elastin block copolymers. See Hurt and Gehrke, *Thermally Associating Polypeptides Designed for Drug Delivery Produced by Genetically Engineered Cells*, J. Phar. Sci. Vol. 96 No. 3 (March 2007), which is incorporated by reference. In general, an elastin mimetic protein is one which has an amino acid sequence and secondary structure derived from native (naturally occurring) elastin. As specifically exemplified herein, the elastin mimetic protein is recombinantly produced in *Escherichia coli*, and it is described in McMillan et al., (1999) Macromolecules 32: 3643-3648; see also Huang et al., (2000) Macromolecules 33: 2989-2997 and McMillan et al., (2000) Macromolecules 33: 4809-4821. The most significant property of the selected thermally gelling polymer is that the gelation point of the polymer is preferably below the melting point (a solid gel) when the PEG-DA or HEMA is polymerized and/or cross-linked.

Preferably, the agarose or gelatin is such that it has a gelling temperature so that living cells may be mixed into a solution of agarose or gelatin at a temperature that does not significantly impair cell viability. As such, the agarose or gelatin preferably does not gel at a temperature higher than that which is compatible with cell viability (because the cells are dispersed in the liquid agarose or gelatin solution), unless it gels slowly. Thus, if the gelation temperature of the agarose or gelatin is above the cell viability temperature, the agarose or gel should not gel more quickly than is necessary to mix the cells into the agarose solution (pre-gel state) at a temperature below the gelation temperature. Typically, for example, the agarose or gelatin should permit mixing (e.g., via gentle mechanical stirring) at a temperature ranging from about 30° C. to 60° C. The solution preferably gels in less than about four hours, more preferably less than one hour, and still most preferably on the order of minutes (typically 1 to 20 minutes, and even 2 to 5 minutes). The solution also preferably takes more than one minute to gel so that there is sufficient time to mix the cells into the solution. The actual gel point temperature is not critical if the gelation is sufficiently slow and as long as the gel is stable at the temperature range of the application and which preserves cell viability. Most preferred agarose gels are the so-called "low-melting" gels as they have gelation temperatures near 37° C. Thus, with such gels, there is less concern about inadvertently contacting the cells with a pre-gel solution that is too hot or that gels before the cells are fully dispersed in the solution. A polymer which forms the more rigid networks is also preferred as this will give the strongest overall gel in the final formulation. A polymer which forms a gel over the widest range of concentrations, from 0.1 to 50 wt % and most preferably between 2 and 10 wt %, is also preferred. This gives the most versatility in formulation and adjustment of properties. Further, is preferable that the physically cross-linked polymer be more rigid than the chemically cross-linked or physically entangled polymer in the overall network as asymmetry in mechanical properties of the two networks comprising the IPN or semi-IPN (one stiff and brittle and one soft and ductile) is believed to yield the most significant increase in mechanical properties.

In the present invention, the chemically cross-linked or physically entangled polymer or copolymer is preferably synthesized from one or more water-soluble vinyl monomer to form either a homopolymer or copolymer. Bi-functional or multi-functional monomers may optionally be added to improve cross-linking and formation of the network. Most preferred chemically cross-linked polymers are synthesized from such as polyethylene glycol diacrylate ("PEG-DA") and 2-hydroxyethyl methacrylate) ("HEMA")

In one aspect, the chemically cross-linked polymer is synthesized from a bi-functional PEG, such as a pre-polymer of PEG-acrylate or PEG-methacrylate having a general formula $CH_2=CR-COO-[CH_2-CH_2-O]_n-COO-CR=CH_2$, wherein R is hydrogen (acrylates), or methyl (methacrylates) and n is the number of ethylene oxide (ethylene glycol) repeating units. The polyethylene component of the bi-functional PEG preferably has weight-average molecular weight in a range of 200 to 50,000 Daltons. Exemplary molecular weights are 200, 300, 500, 700, 1000, 2000, 3000, 4000, 5000, 6000, 7000, 10,000, 20,000, 30,000, 40,000, and 50,000 Daltons. The number of ethylene oxides contained in the oligomer preferably ranges between 4 to 1000 or more. Other suitable multi-functional PEG compounds include PEG triacrylate. Other photopolymerizable substituents preferably include acrylates, diacrylates, oligoacrylates, dimethacrylates, or oligomethacrylates, and other biologically acceptable photopolymerizable groups.

The bi-functional PEG (e.g., PEG-DA) is polymerized or cured, for example, using an initiator which is activated by UV radiation (UV initiators), visible light (light initiators), heat (thermal initiators), or chemical initiators. Examples of appropriate initiators include acetophenone, 2,2-dimethoxy-2-phenol-acetophenone ("DMPA") (UV initiators), camproquinone, ethyl-4-N,N,-dimethyl aminobenzoate (light initiators), benzoyl peroxide (thermal initiator), or ammonium persulfite (chemical initiator). A preferred initiator for PEG-DA is 4-(2-hydroxyethoxy)phenyl-(2-hydroxy-2-propyl)ketone (Irgacure 2959). The preferred initiator for PHEMA synthesis is alpha-ketoglutaric acid (KGA). As a result of the curing process, PEG-diacrylate or PEG-dimethacrylate will at least partially cross-link and at least partially physically entangle within the agarose or gelatin gel.

Polymerization of HEMA results in a linear polymer known as poly(2-hydroxyethyl methacrylate) ("PHEMA"). To form a cross-linked network, a bi-functional or multi-functional (e.g., multivinyl) crosslinker is added. A preferred cross-linker is N,N'-methylene-bis-acrylamide. It will be appreciated that if the PHEMA grows to a sufficient molecular weight, it can penetrate and become entangled within the physically cross linked polymer (e.g., the agarose or gelatin), without the addition of the cross-linker. Thus, the HEMA will form a linear PHEMA polymer that, when sufficiently large, is physically entangled within the agarose or gelatin gel, and with an optional suitable cross-linker will also form a chemically cross-linked polymer within the gel. The former material is a semi-IPN and the latter material is an IPN.

The resulting hydrogel network having the living cells encapsulated therein preferably is comprised of 0.1 to 50 wt % physically cross-linked polymer and about 2 to 90 wt % of the chemically polymerized and/or cross-linked polymer or copolymer and the remainder water (typically at least 10% water). For example, the PEG-DA:agarose ratio preferably ranges between 50:1 and 1:2, and still more preferably between about 20:1 and 5:1, and most preferably about 10:1

The hydrogel networks of the present invention are well adapted for encapsulating cells. For example, typically about $10^6$ to $10^8$ cells/cm$^3$ are encapsulated within a network comprised of PEG-DA and agarose.

In specific embodiments, the cells are mammalian cells, preferably human cells. In one aspect, the cells are selected from the group consisting of connective tissue cells, organ cells, muscle cells, nerve cells, and any combination thereof. In more specific embodiments, the cells are selected from the group consisting of tenocytes, fibroblasts, ligament cells, endothelial cells, lung cells, epithelial cells, smooth muscle cells, cardiac muscle cells, skeletal muscle cells, islet cells, nerve cells, hepatocytes, kidney cells, bladder cells, urothelial cells, chondrocytes, and bone-forming cells. In some embodiments in which encapsulated cells are non-proliferating cells, the non-proliferating cells may be selected from the group consisting of pancreatic islets, hepatic cells, neural cells, renal cortex cells, vascular endothelial cells, thyroid and parathyroid cells, adrenal cells, thymic cells, ovarian cells, and chondrocytes. Further, the cells may be stem cells, including but not limited to, bone marrow-derived stem cells, embryonic stem cells, umbilical cord-derived stem cells, placenta-derived stem cells, and amniotic fluid-derived stem cells.

The living cells may be engineered to express a target gene product which is biologically active which provides a chosen biological function, which acts as a reporter of a chosen physiological condition, which augments deficient or defective expression of a gene product, or which provides an anti-viral, anti-bacterial, anti-microbial, or anti-cancer activity. In accordance with the present invention, the target gene product may be a peptide or protein, such as an enzyme, hormone, cytokine, antigen, or antibody, a regulatory protein, such as a transcription factor, or DNA binding protein, a structural protein, such as a cell surface protein, or the target gene product may be a nucleic acid such as a ribosome or antisense molecule. The target gene products include, but are not limited to, gene products which enhance cell growth. For example, the genetic modification may upregulate an endogenous protein, introduce a new protein, or regulate ion concentration by expressing a heterologous ion channel or altering endogenous ion channel function. Examples include, but are not limited to engineered tissues that express gene products which are delivered systemically (e.g., secreted gene products such as proteins including growth factors, hormones, Factor VIII, Factor IX, neurotransmitters, and enkephalins).

In some instances, peptide sequences, growth factors, or hormones may be incorporated within the hydrogel network in order to assist with cell growth and viability. Biodegradable sequences can be incorporated into the networks themselves by functionalizing a degradable sequence with polymerizable groups, most notably acrylate or methacrylate groups, and including this as a comonomer during network polymerization. A chemically degradable link (e.g., hydrolytically unstable) may cause the network to chemically degrade over time, which can lead to the body's elimination of the hydrogel over time. An enzymatically degradable link may allow degradation to occur when cells reach a certain metabolic state where they secrete such a degradative enzyme. This may allow cells to migrate through the network as they proliferate and possibly replace the gel with native extracellular matrix.

First of all, this hydrogel network has a compression stress at failure (fracture or rupture) of preferably at least 1 MPa. In addition, the gel has a tensile stress at failure of preferably at least 0.1 MPa.

Furthermore, the hydrogel according to this invention has a water content of 10% or more, more preferably 50% or more, and even more preferably 85% or more. Thus, allowing the gel to have a large amount of water will improve flexibility and permeability for soluble components such as nutrients, waste products, oxygen, growth factors, drugs and so forth. The upper limit of the water content is not particularly defined, but is usually 99.9% or less, preferably 99% or less, and more preferably 95% or less for the purpose of retaining mechanical strength, etc.

Depending on the cell type, the hydrogel networks of the present invention may be injected or implanted into any acceptable tissue, including but not limited to, cartilage, bone, tendon, ligament, intervertebral disc, meniscus, bladder, cardiac muscle, skeletal muscle, myocardium, fascia, adipose tissue, nerve, heart valve, intestine, lung, blood vessels, as well as organs such as kidney, liver, pancreas, stomach, and colon.

In some embodiments, the hydrogel networks are configured and dimensioned to be mounted in both an area of damaged or destroyed tissue that has been removed, and in an adjacent healthy area of tissue. When the hydrogel networks containing the encapsulated living cells is placed in an area of removed tissue, communication is established between the healthy tissue and the damaged tissue area via the three-dimensional tissue scaffold (the hydrogel network), permitting vascular invasion and cellular migration. The hydrogel networks containing the encapsulated cells may be implanted using standard surgical methods or can be implanted using less-invasive or minimally invasive methods such as arthroscopy or laparoscopy. The hydrogel networks containing the encapsulated cells may be attached in place using a variety of methods including but not limited to surgical sutures, screws, nails, tacks, glues, adhesives, or cements or simply being press-fitted into place.

Further with respect to the disclosed subject matter, a preferred subject is a vertebrate subject. A preferred vertebrate is warm-blooded; a preferred warm-blooded vertebrate is a mammal. A preferred mammal is most preferably a human. As used herein, the term "subject" includes both human and animal subjects. Thus, veterinary therapeutic uses are provided in accordance with the presently disclosed subject matter. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses.

The present invention is further illustrated with non-limiting examples described below.

EXAMPLE 1

Agarose/PHEMA Hydrogel Synthesis and Mechanical Testing

In this example, a hydrogel network formed from agarose as the rigid polysaccharide component and poly(2-hydroxymethacrylate) ("PHEMA") as the ductile polymer phase was prepared, and compared to agarose and PHEMA gels alone. In general, agarose formed a physical gel upon cooling from an aqueous solution. The agarose gel was then soaked a solution comprising a HEMA monomer with a photoinitiator, with and without the crosslinker N,N'-methylene-bis-acrylamide. After equilibration, the HEMA monomer was photopolymerized with UV light. The hydrogel network was then subjected to both transient (ultimate) and dynamic tensile tests and compared the single polymer gels with the semi-IPN (uncrosslinked PHEMA) and IPN (cross-linked PHEMA).

More specifically, agarose as a dry powder (>99% pure with a gelling temperature of 40-43° C. lot number 456755/1), the monomer 2-hydroxyethyl methacrylate (HEMA) (>99% pure), the initiator α-ketoglutaric acid (KGA) (>99% pure) and the cross-linker methylene-bis-acrylamide (MBA) (99% pure) were used as received from Sigma Aldrich (St. Louis, Mo.). To make the agarose gel, agarose powder was added to 5 mL of D.I.U.F. water to yield a 2 wt % agarose solution. The solution was heated and stirred on a hotplate with a magnetic stirrer until dissolution occurred and boiling began. About 170 µl of the solution were then immediately pipetted into dog-bone shaped wells in silicon rubber molds. The agarose gels were allowed to cure for 24 hours.

To prepare the IPNs, the agarose gel was then soaked in a 2.5 M solution of HEMA monomer in water with MBA to create a 0.1% mol cross-linker to monomer ratio. To obtain a semi-IPN, no cross-linker was added. About 0.17 mL agarose gels were soaked in 10 mL of deoxygenated monomer solution, also containing 0.1% mol of the photoinitiator alpha-ketoglutaric acid (KGA). The dog bone-shaped agarose gel was then removed from the excess solution and given 24 hours to equilibrate in a sealed glass vial. The polymerization reaction of HEMA was then immediately initiated using the 8-Watt, 254 nm Spectrolinker Microprocessor-Controlled UV Crosslinker XL-1000 (Spectronics Corp.) for about three hours. After polymerization of the secondary entangled polymer or crosslinked network within the primary one, the hydrogel networks were placed in excess D.I.U.F. water for approximately five days to leach unreacted material from the hydrogel network.

A similar procedure was used to synthesize PHEMA gels except that the HEMA plus MBA solution was poured directly into the mold and photopolymerized.

Figure 1:
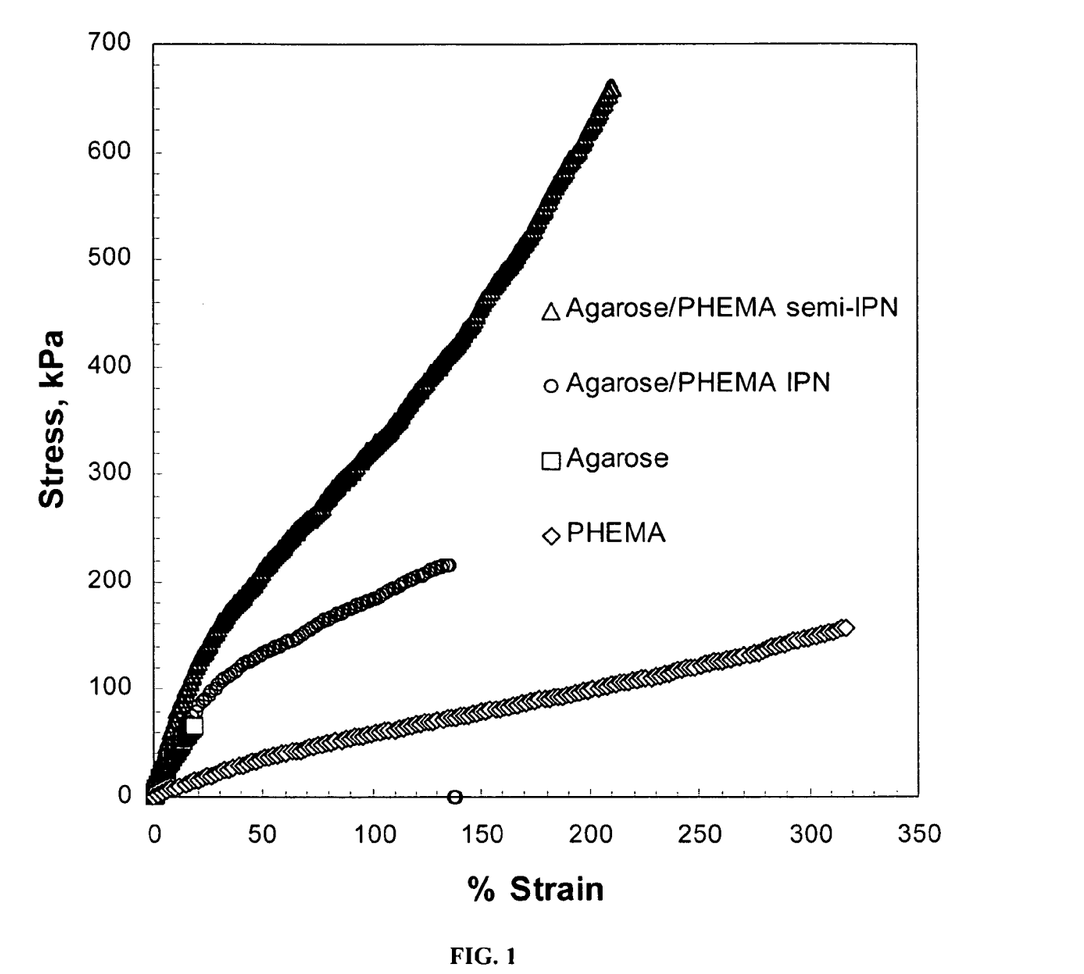
FIG. 1 shows the results of tensile tests of the different agarose and PHEMA gels alone and in combination. The figure shows that the combination of a brittle (agarose) and ductile (PHEMA) polymer into a semi-interpenetrating network greatly enhances the strength and toughness achieved by either network alone. The toughness of the semi-IPN is 800±84 kPa, while it is only 240±100 kPa for PHEMA and 10±4 kPa for agarose. The performance of the IPN is not as great as the semi-IPN, with a toughness of only 190±150 kPa, but the strength (e.g., Young's modulus) is still much better than PHEMA and fracture strain much better than agarose.
Figure 2:
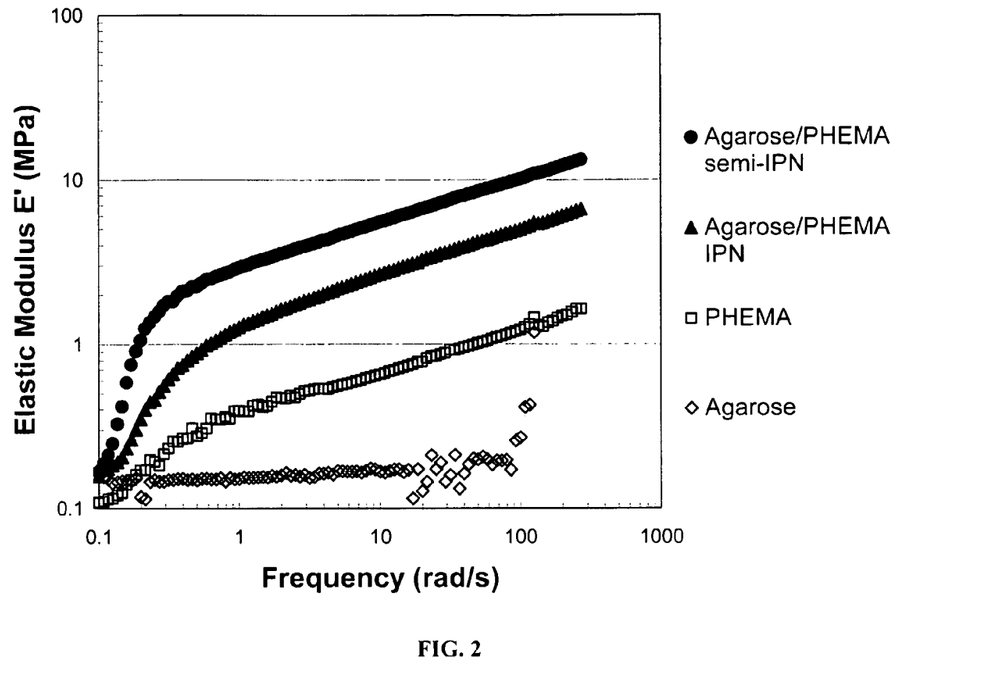
FIG. 2 shows the elastic (storage) modulus during frequency sweep experiments in tensile mode of different agarose and PHEMA gels alone and in combination. As in FIG. 1, the performance of the semi-IPN is far superior to the single-network gels, as is the IPN, although to a lesser extent. The significant frequency dependence indicates that the lightly crosslinked PHEMA with N,N'-methylene-bis-acrylamide and the semi-IPN are not fully elastic and have significant viscous components (tan $\delta$=0.37±0.02 for the semi IPN, 0.33±0.1 for PHEMA but only 0.05±0.02 for well-crosslinked though dilute agarose).

The mechanical properties of these gels were measured using an RSA III Dynamic Mechanical Analyzer (TA Instruments, New Castle, Del.) in tensile mode. The dogbone shaped gel samples were mounted between sandpaper-covered grips for both transient and dynamic measurements experiments. The transient (or ultimate) experiments measured the force required to stretch the sample at 1 mm/s until failure. Frequency sweep experiments were performed with a fixed 0.2% strain as the oscillatory frequency increased from 0.1 to approximately 1000 rad/s. The results for the ultimate tensile tests are shown in FIG. 1 and for the dynamic tensile tests in FIG. 2. These results clearly demonstrate the superior performance of the hybrid material relative to the individual polymers. The frequency dependence and the significant tan δ for both the semi-IPN and IPN indicate that these materials have significant viscous components to their mechanical behavior. The frequency independence of E' and the low tan δ of the agarose indicates that it behaves as a well crosslinked elastic solid, though because it is 98% water, its modulus is lesser than the PHEMA. The IPN of agarose and crosslinked PHEMA also has superior properties to the single-component gels, but less of an improvement is seen since the fracture strain has not increased quite as much as it did in the semi-IPN.

EXAMPLE 2

Agarose/PEG-DA Hydrogel Synthesis and Mechanical Testing

In this example, a hydrogel network formed from agarose as the rigid polysaccharide component and PEG-DA as the chemically cross-linked component was prepared, and compared to agarose and PEG-DA gels alone.

More specifically, agarose powder (Type VII [gelling temperature<30° C., melting temperature>60° C.] cell culture-tested, Sigma Aldrich, St. Louis, Mo.) was dissolved in hot water to form a clear, 2 wt % solution and about 0.4 mL aliquots were added to cylindrical molds of silicon rubber to form disks upon gelation. They were refrigerated at about 4° C. for 24 hours (without cells). A solution of 23 wt % PEG-DA (nominal molecular weight 750, Sigma Aldrich, St. Louis, Mo.) and 0.1 wt % Irgacure 2959 photoinitiator (Ciba Specialty Chemicals, Tarrytown, N.Y.) was then prepared. Agarose gel disks were then placed in excess PEG-DA solution and permitted to soak for about 24 hours to absorb PEG-DA. After about 24 hours, the gel was removed from the solution and placed in the photo-crosslinker device (the 8-Watt, 254 nm Spectrolinker Microprocessor-Controlled UV Crosslinker XL-1000 manufactured by Spectronics Cooperation) for about five minutes (254 nm, 3000 $\mu W/cm^2$). The gel was removed from the photo-crosslinker device, placed in water, and allowed to equilibrate. The final composition of the IPN formed had about 80% water and a PEG-DA:agarose ratio of about 10:1. It is theorized that IPN hydrogels have favorable mechanical properties with an excess of the second, more ductile network (PEG-DA in this case) relative to the first, more rigid network (agarose in this case).

Figure 3:
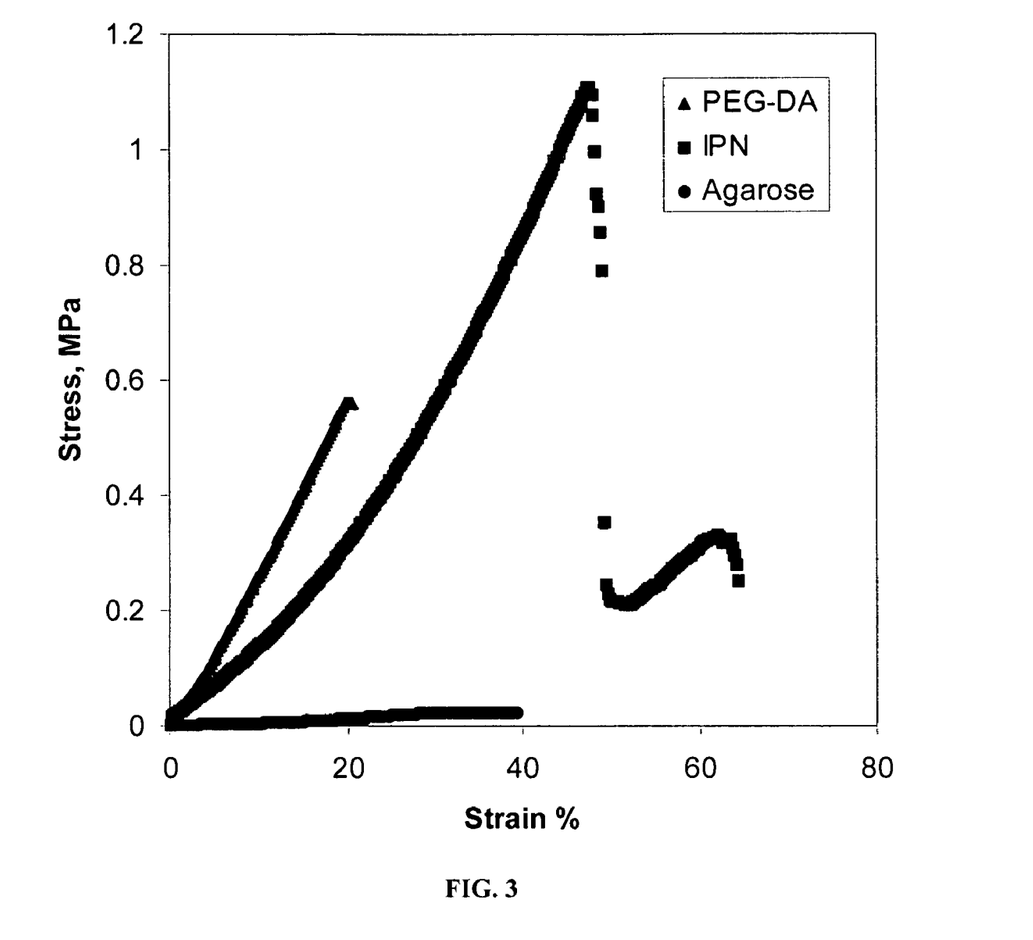
FIG. 3 shows the stress-strain profile of PEG-DA and agarose gels compared to a PEG-DA/agarose hydrogel IPN network of the present invention.
Figure 4:
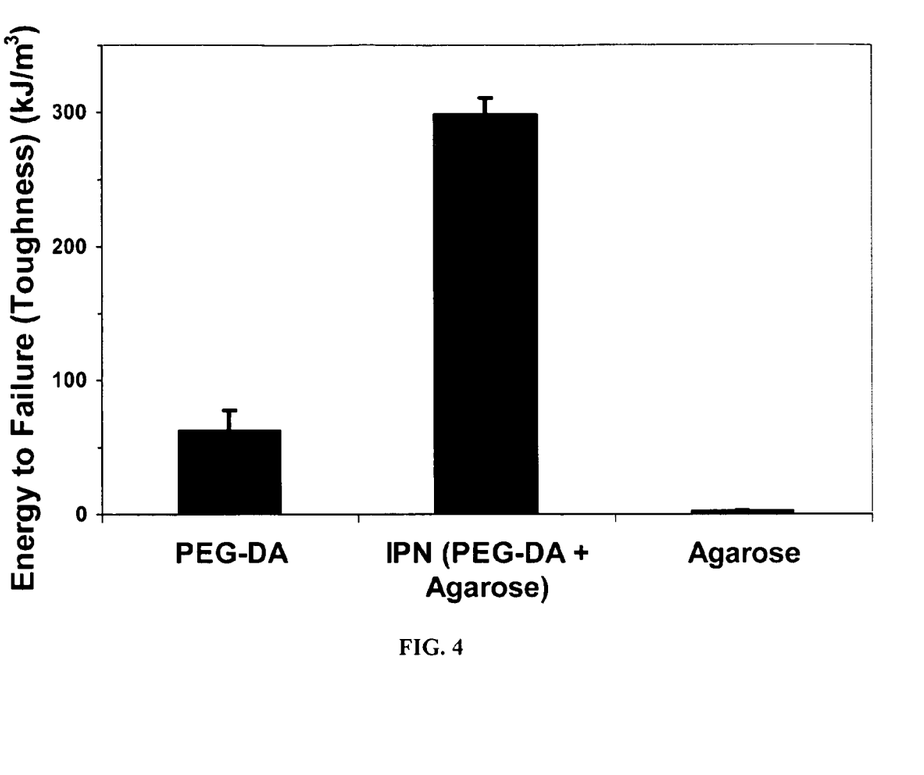
FIG. 4 shows the energy of failure or toughness for PEG-DA and agarose gels compared to a PEG-DA/agarose hydrogel network of the present invention.

The resulting hydrogel network was tested for mechanical strength. FIG. 3 shows the stress-strain curve for the PEG-DA/agarose network compared to PEG-DA and agarose single-network gels of the same polymer concentrations as in the IPN. This experiments were carried out on gels disks roughly 6.25 mm in diameter and 1.75 mm in thickness in a compression mode at a strain rate of 0.05 mm/s at room temperature using a RSA III Dynamic Mechanical Analyzer (TA Instruments, New Castle, Del.). The data shows that the IPN has a fracture stress (1.1 MPa) and fracture strain (53%) leading to a toughness of 300 $kJ/m^3$, which is 100 times greater than that of the agarose itself and 5 times greater than that of the PEG-DA network (FIGS. 3 and 4). Although the lower toughness of the agarose is partially explained by its high water content (98%), the water contents of PEG-DA and the IPN are nearly the same (80% and 75%, respectively). This data clearly shows the superior performance of the IPN over both agarose and PEG-DA gels. The latter gels have already been used in a variety of biomedical applications including tissue engineering, so the potential of these novel IPNs in practical applications is clearly demonstrated.

Importantly, the agarose and PEG-DA were immiscible in a common solvent. Thus, it was not possible to mix the agarose and PEG-DA to form the IPN in a single step because the agarose solution would not dissolve in the PEG-DA solution and thus a poor quality, heterogeneous gel was obtained in a single-step synthesis. Also, since these polymers are non-ionic, their properties will not be significantly affected by pH or ionic strength.

EXAMPLE 3

Cell Encapsulation in Agarose-PEG-DA IPN

In this example, chondrocytes were encapsulated in a hydrogel comprising agarose and a chemically crosslinked polymer or copolymer synthesized from PEG-DA. To isolate the chondrocytes, articular cartilage was obtained under aseptic conditions from the ankle of six-week old female pigs. Cells were harvested within six hours of slaughter. The cartilage was digested in collagenase type II (Worthington, Biochemical Corp., Lakewood, N.J.) in culture medium. The medium was Dulbecco's Modified Eagle Medium (DMEM) with 4.5 g/L D-glucose 10% fetal bovine serum, 1% non-essential amino acids, ascorbic acid (50 µg/mL), and 1% penicillin-streptomycin-fungicide (Fungizone) (Cambrex). After suspension in phosphate buffered saline (PBS), the cells were encapsulated in agarose at a concentration of approximately $1 \times 10^6$ cells/mL as described below.

To synthesize the hydrogel network agarose/PEG-DA having living cells encapsulated therein, the chondrocytes were encapsulated in a thermally gelled agarose mold as discussed in Example 2 except that the extended curing time at 4° C. was not used. Specifically, an agarose solution was prepared at about 40° C. to 60° C., and then allowed to cool to about 37° C., wherein chondrocytes were slowly mixed in over a period of a few minutes to a final concentration around $1\times10^6$ cells/mL. The mixture was then held at about 37° C. until the gel formed, thus encapsulating the cells. Following encapsulation, the constructs were incubated in well plates with DMEM culture medium at 37° C. and 5% $CO_2$ in a humid environment for 24 hours. The agarose gel having the chondrocytes encapsulated therein was then soaked in a 23 wt % solution of PEG-DA (MW 700) in pH 7.4 phosphate buffered saline (PBS) and the photoinitiator Irgacure 2959 for about 24 hours at 37° C. in an incubator with an atmospheric $CO_2$ concentration of 5%. The PEG network was formed upon irradiation at 254 nm for about five minutes in the Spectrolinker device described earlier.

Figure 5:
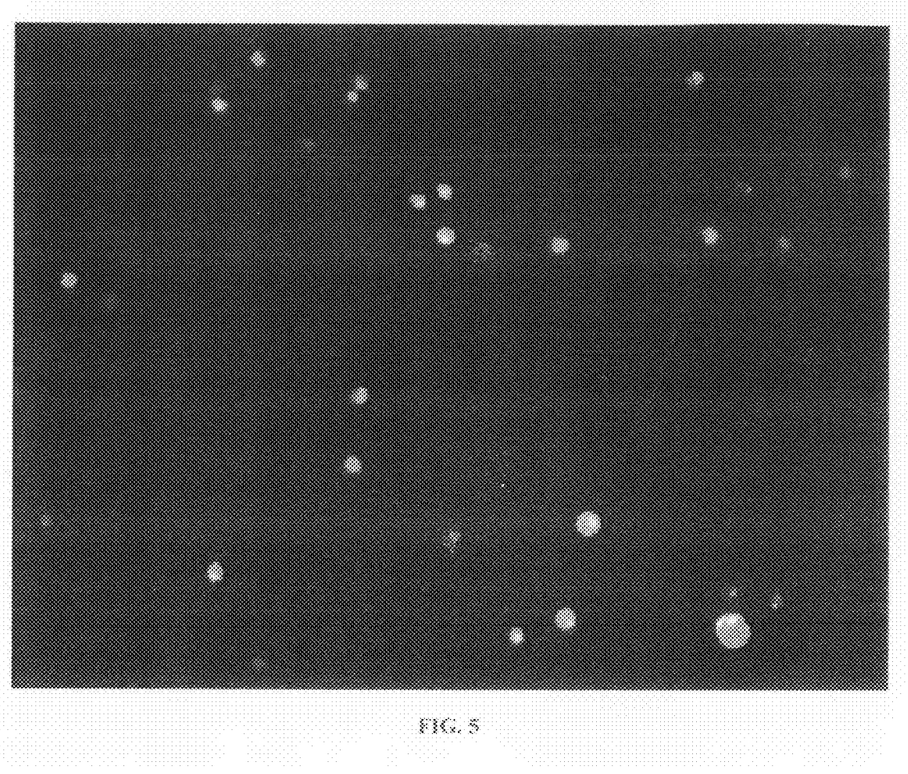
FIG. 5 shows the results of the live-dead assay (green=living cells, red=dead cells) for the PEG-DA agarose network. The cells were cultured in the network for two days.

Cell viability was determined using the LIVE/DEAD Viability/Cytotoxicity Kit for mammalian cells (Molecular Probes, USA). Constructs were incubated in PBS containing 4 μM ethidium homodimer (EthD-1) and 2 μM calcein AM for thirty minutes at room temperature. Cell viability was determined using fluorescence microscopy. Living cells stained with calcein AM appeared green in color, while dead cells stained with EthD-1 appeared red in color. The results are shown in FIG. 5 and clearly show that a significant population of cells are alive following encapsulation.

Figure 6:
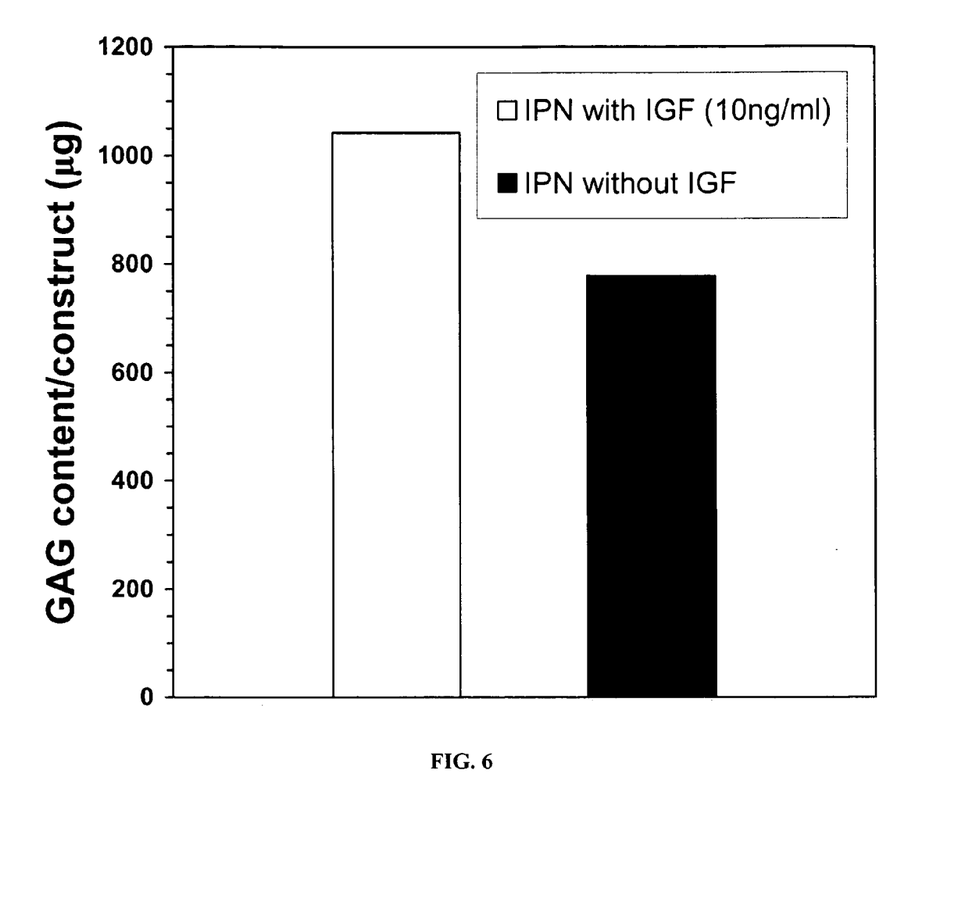
FIG. 6 shows the biosynthesis of glycosaminoglycans by chondrocytes encapsulated in agarose/PEG-DA hydrogel network of the present invention. This demonstrates that the cells not only survive the synthesis, but also live and thrive in the gel for an extended period of time (four weeks).

Furthermore, it has been shown that the cells encapsulated in the gels are not simply alive, but are also thriving, as they also produce native extracellular matrix components. IPNs were synthesized from 2% agarose (Sigma, Type VII Agarose, Cell Culture Tested) and PEG-DA (Aldrich, $M_n$=about 700 Da). The agarose gel was formed by thermal gelation in a well plate, with porcine ankle chondrocytes (passage 1, 7.7M cells/mL) being added to the agarose gel shortly before its gelling temperature of about 37° C. The agarose gel (with cells) was soaked in a solution of PEG-DA, PBS, and the photocrosslinker Irgacure 2959 (Ciba) for 24 h. The IPN was formed upon irradiation of the agarose gel for five minutes at 254 nm to create final construct dimensions of 6×3.1 mm (diameter×thickness). Constructs were cultured for 4 wks with the medium changed every 48 hours. The media consisted of Dulbecco's Modified Eagle Medium (DMEM)-high glucose (4.5 g/L d-glucose) with 50 mg/mL ascorbic acid, 10% fetal bovine serum (FBS), 1% non-essential amino acids (NEAA), and 1% penicillin-streptomycin-fungizone, with or without 10 ng/mL insulin like-growth factor-I (IGF-I). After 4 weeks, a tremendous quantity of GAGs were observed (measured by DMMB assay), with average values (n=3) of 1042 and 778 μg GAG per construct for the IGF-I and control groups, respectively (FIG. 6).

From the foregoing it will be seen that this invention is one well adapted to attain all ends and objectives herein-above set forth, together with the other advantages which are obvious and which are inherent to the invention. Since many possible embodiments may be made of the invention without departing from the scope thereof, it is to be understood that all matters herein set forth or shown in the accompanying drawings are to be interpreted as illustrative, and not in a limiting sense. While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

What is claimed and desired to be secured by Letters Patent is as follows:

1. A method for preparing a hydrogel network having living cells encapsulated therein comprising the steps of:
    forming a solution of a thermally gelling polysaccharide or protein at a temperature in which the living cells are viable and dispersing the cells therein;
    cooling the thermally gelling polysaccharide or protein solution down to or below its gelation temperature in which the living cells are also viable to cause gelation and form a polysaccharide or protein gel and to encapsulate the cells in said gel;
    contacting the polysaccharide or protein gel having the living cells encapsulated therein with a solution comprising one or more water-soluble vinyl monomers for a sufficient period of time to disperse the one or more water-soluble vinyl monomers within the gel; and then
    polymerizing and/or cross-linking the one or more water-soluble vinyl monomers within said gel.

2. The method of claim 1 wherein said thermally gelling polysaccharide or protein is selected from the group consisting of agarose, gelatin, kappa-carrageenan, iota-carrageenan, elastin-mimetic polymers, and silk-elastin block copolymers.

3. The method of claim 1 wherein said thermally gelling polysaccharide or protein solution is an agarose or gelatin solution having a gelation temperature of about 20° C. to 60° C., and wherein said cooling step forms an agarose or gelatin gel.

4. The method of claim 3 wherein said contacting step comprises soaking said agarose or gelatin gel in a solution comprising polyethylene glycol diacrylate ("PEG-DA") or polyethylene dimethacrylate ("PEG-DMA") or 2-hydroxyethyl methacrylate ("HEMA") as said one or more water-soluble vinyl monomers.

5. The method of claim 1 wherein said living cells are chondrocytes.

6. The method of claim 1 wherein said thermally gelling polysaccharide or protein solution further comprises a photoinitiator or said solution comprising the one or more water-soluble vinyl monomers further comprises a photoinitiator.

7. The method of claim 1 wherein said thermally gelling polysaccharide or protein solution further comprises a chemically or enzymatically degradable monomer or said solution comprising the one or more water-soluble vinyl monomers further comprises a chemically or enzymatically degradable monomer.

8. The method of claim 3 further comprising a crosslinker which is a multifunctional vinyl monomer in the agarose or gelatin solution.

9. The method of claim 8 wherein said multifunctional vinyl monomer comprises N,N'-methylenebisacrylamide.

10. The method of claim 1 wherein said thermally gelling polysaccharide or protein is selected from the group consisting of agarose, gelatin, kappa-carrageenan, iota-carrageenan, elastin-mimetic polymers, and silk-elastin block copolymers; and further comprising polymerizing and/or cross-linking said vinyl monomers within said gel by irradiating said gel for less than ten minutes.

11. The method according to claim 1 wherein said one or more water soluble vinyl monomers comprises a bi-functional polyethylene glycol component and wherein said thermally gelling polysaccharide comprises agarose.

12. The method according to claim 11, wherein the bi-functional polyethylene glycol component is selected from the group consisting polyethylene glycol diacrylate ("PEG-DA") or polyethylene dimethacrylate ("PEG-DMA").

13. The method according to claim 11, wherein the polyethylene glycol component of the bi-functional polyethylene glycol component has a molecular weight between 200 and 50,000 Daltons.

14. The method according to claim 11 wherein the hydrogel network has a water content of 10% or more.

15. The method according to claim 11 wherein the hydrogel network has a compression stress at failure of at least 1 MPa.

16. The method according to claim 11 wherein the hydrogel network has a tensile stress at failure of at least 1 MPa.

17. The method according to claim 11 in which the one or more water soluble vinyl monomers is PEG-DA, and wherein said PEG-DA:agarose ratio is between about 20:1 and 2:1.

18. The method of claim 1 wherein said one or more water-soluble vinyl monomers comprises PEG-DA or HEMA.

19. The method according to claim 1, wherein said one or more water-soluble vinyl monomers comprises PEG-DA, and wherein said polyethylene glycol component of the PEG-DA has a molecular weight between 200 and 50,000 Daltons.

20. The method according to claim 1 wherein said living cells are encapsulated within said hydrogel network at a density ranging between about 1,000,000 cells/cm$^3$ and 50,000,000 cells/cm$^3$.

21. The method of claim 1 wherein said solution comprising said one or more water-soluble vinyl monomers further comprises a cross-linker.

* * * * *